(12) United States Patent
Santhany et al.

(10) Patent No.: US 9,187,403 B2
(45) Date of Patent: Nov. 17, 2015

(54) PROCESS FOR SEPARATING ONE OR MORE ALIPHATIC DIAMINES FROM REDUCTIVE AMINATION REACTION SOLVENTS AND IMPURITIES

(75) Inventors: Stacie Santhany, Auburn, MI (US); Patrick Ho Sing Au-Yeung, Midland, MI (US); Gerald W. Dare, Pearland, TX (US); Shawn D. Feist, Midland, MI (US); Barry B. Fish, Lake Jackson, TX (US); Daniel A. Hickman, Midland, MI (US); David Jean, Friendswood, TX (US); Erich J. Molitor, Midland, MI (US); Abraham D. Schuitman, Midland, MI (US); Todd William Toyzan, Freeland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/383,325

(22) PCT Filed: Jul. 30, 2010

(86) PCT No.: PCT/US2010/043915
§ 371 (c)(1),
(2), (4) Date: Jan. 10, 2012

(87) PCT Pub. No.: WO2011/014780
PCT Pub. Date: Feb. 3, 2011

(65) Prior Publication Data
US 2012/0116123 A1 May 10, 2012

Related U.S. Application Data

(60) Provisional application No. 61/230,300, filed on Jul. 31, 2009.

(51) Int. Cl.
C07C 209/00 (2006.01)
C07C 209/86 (2006.01)

(52) U.S. Cl.
CPC ........... *C07C 209/86* (2013.01); *C07C 2101/14* (2013.01)

(58) Field of Classification Search
CPC .............................. C07C 209/86; C07C 211/28
See application file for complete search history.

(56) References Cited

U.S. PATENT DOCUMENTS 3,012,994 A 12/1961 Bell et al.
3,143,570 A 8/1964 Caldwell et al.
(Continued)

FOREIGN PATENT DOCUMENTS

EP 0703213 A2 3/1996
EP 1348688 A1 10/2003
JP 07188126 A 7/1995

OTHER PUBLICATIONS

EP Office Action dated Dec. 11, 2013; from EP counterpart Application No. 10 739 811.7.
(Continued)

*Primary Examiner* — Clinton Brooks (57) ABSTRACT

The instant invention provides a process for separating one or more aliphatic diamines from reductive amination reaction solvents and impurities, and aliphatic diamines obtained via such a process. The process for separating one or more aliphatic diamines from reductive amination reaction solvents and impurities according to the instant invention comprises the steps of: (1) feeding one or more cycloaliphatic cyanoaldehydes, hydrogen, ammonia, and optionally one or more solvents into a continuous reductive amination reactor system; (2) contacting said one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig; (3) thereby forming a product mixture comprising one or more cycloaliphatic diamines, optionally one or more bicyclic by-products, optionally one or more cycloaliphatic aminonitriles, optionally one or more cycloaliphatic aminoalcohols, optionally one or more oligomeric by-products, ammonia, water, hydrogen, and optionally one or more solvents; (4) removing said product mixture from the reactor system; (5) removing at least a portion of said ammonia, said hydrogen, or mixture thereof from said product mixture via distillation; (6) removing at least a portion of said water and said one or more optional solvents via distillation; (7) removing at least a portion of one or more optional bicyclic by-products via distillation; (8) removing one or more optional cycloaliphatic aminonitriles, one or more optional cycloaliphatic aminoalcohols, one or more optional oligomeric by-products via distillation; and (9) thereby separating said one or more cycloaliphatic diamines from said product mixture.

10 Claims, 4 Drawing Sheets (56) References Cited

U.S. PATENT DOCUMENTS

| | | | |
|---|---|---|---|
| 6,139,693 | A | 10/2000 | Bassler et al. |
| 6,252,121 | B1 | 6/2001 | Argyropoulos et al. |
| 6,462,220 | B1 | 10/2002 | Luyken et al. |
| 2005/0215824 | A1 | 9/2005 | Amakawa et al. |
| 2006/0058555 | A1 | 3/2006 | Ostermaier |
| 2008/0167499 | A1 | 7/2008 | Molitor et al. |
| 2009/0048466 | A1 | 2/2009 | Lettmann et al. |

OTHER PUBLICATIONS

Instructions to EP Office Action dated Dec. 31, 2013; from EP counterpart Application No. 10 739 811.7.
EP Response to Office Action dated Jan. 10, 2014; from EP counterpart Application No. 10 739 811.7.
Chinese Second Office Action dated Nov. 4, 2013; from Chinese counterpart Application No. 201080037245.1.
Instructions to Chinese Office Action dated Jan. 8, 2014; from Chinese counterpart Application No. 201080037245.1.
Chinese Response to Office Action dated Jan. 19, 2014; from Chinese counterpart Application No. 201080037245.1.
Instructions to Chinese Office Action dated Aug. 18, 2014; from Chinese counterpart Application No. 201080037245.1.
Response to Chinese Office Action dated Aug. 22, 2014; from Chinese counterpart Application No. 201080037245.1.
Japanese Response to Office Action dated Jul. 23, 2014; from Japanese counterpart Application No. 2012-523092.
Chinese Office Action dated May 9, 2014; from Chinese counterpart Application No. 201080037245.1.
Japanese Office Action dated May 7, 2013; from Japanese counterpart Application No. 2012-523092.
Instructions to Japanese Office Action dated Jul. 10, 2014; from Japanese counterpart Application No. 2012-523092.
Communication for Art. 94(3) EPC dated Dec. 12, 2014 for counterpart EP Application No. 10739811.7, 2 pages.
Japanese Decision of Rejection dated Feb. 3, 2015 for counterpart Japanese Application No. 2012-523092, 1 page.
Notification of Reexamination dated Mar. 30, 2015 for counterpart Chinese Application No. 201080037245.1, 15 pages.
EPO Response to Office Action dated Dec. 12, 2014 for counterpart EPO Application No. 10739811.7, 12 pages.
Japanese Response to Office Action dated May 15, 2015; from Japanese counterpart Application No. 2012-523092.
Gomez, The Reductive Amination of Aldehydes and Ketones and the Hydrogenation of Nitriles, Advanced Synthesis & Catalysis, vol. 344 No. 10 p. 1037-1057, 2002.
PCT/US2010/043915, International Search Report and Written Opinion.
PCT/US2010/043915, International Preliminary Report on Patentability.
Response to Chinese Office Action filed on Jul. 1, 2015; for counterpart Chinese Application No. 201080037245.1, 8 pages.

PROCESS FOR SEPARATING ONE OR MORE ALIPHATIC DIAMINES FROM REDUCTIVE AMINATION REACTION SOLVENTS AND IMPURITIES

CROSS-REFERENCE TO RELATED APPLICATIONS

This application is a non-provisional application claiming priority from the U.S. Provisional Patent Application No. 61/230,300, filed on Jul. 31, 2009, entitled "PROCESS FOR SEPARATING ONE OR MORE ALIPHATIC DIAMINES FROM REDUCTIVE AMINATION REACTION SOLVENTS AND IMPURITIES," the teachings of which are incorporated by reference herein, as if reproduced in full hereinbelow.

FIELD OF INVENTION

The instant invention relates to a process for separating one or more aliphatic diamines from reductive amination reaction solvents and impurities.

BACKGROUND OF THE INVENTION

The aliphatic diamine reaction mixtures typically include many impurities. Such impurities are undesirable and should be separated from the desired diamine products to meet the certain required specifications. Despite the research effort to improve the process for isolation of desired diamine products, there is still a need for a method by which cycloaliphatic bis(aminomethyl) compounds can be prepared economically and in high yields.

SUMMARY OF THE INVENTION

The instant invention provides a process for separating one or more aliphatic diamines from reductive amination reaction solvents and impurities, and aliphatic diamines obtained via such a process.

In one embodiment, the instant invention provides a process for separating one or more aliphatic diamines from reductive amination reaction solvents and impurities comprising the steps of: (1) feeding one or more cycloaliphatic cyanoaldehydes, hydrogen, ammonia, optionally water, and optionally one or more solvents into a continuous reductive amination reactor system; (2) contacting said one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig; (3) thereby forming a product mixture comprising one or more cycloaliphatic diamines, optionally one or more bicyclic by-products, optionally one or more cycloaliphatic aminonitriles, optionally one or more cycloaliphatic aminoalcohols, optionally one or more oligomeric by-products, ammonia, water, hydrogen, and optionally one or more solvents; (4) removing said product mixture from the reactor system; (5) removing at least a portion of said ammonia, said hydrogen, or mixture thereof from said product mixture via distillation; (6) removing at least a portion of said water and said one or more optional solvents via distillation; (7) removing at least a portion of one or more optional bicyclic by-products via distillation; (8) removing one or more optional cycloaliphatic aminonitriles, one or more optional cycloaliphatic aminoalcohols, one or more optional oligomeric by-products via distillation; and (9) thereby separating said one or more cycloaliphatic diamines from said product mixture.

In an alternative embodiment, the instant invention further provides one or more aliphatic diamines produced according to the preceding process.

In an alternative embodiment, the instant invention provides a process for separating one or more aliphatic diamines in accordance with any of the preceding embodiments, except that one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof.

In an alternative embodiment, the instant invention provides a process for separating one or more aliphatic diamines in accordance with any of the preceding embodiments, except that one or more cycloaliphatic diamines are diamines selected from the group consisting of 1,3-bis(aminomethyl) cyclohexane, 1,4-bis(aminomethyl)cyclohexane, combinations thereof, and mixtures thereof.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

The instant invention provides a process for separating one or more aliphatic diamines from reductive amination reaction solvents and impurities, and aliphatic diamines obtained via such a process. The process for separating one or more aliphatic diamines from reductive amination reaction solvents and impurities according to the instant invention comprises the steps of: (1) feeding one or more cycloaliphatic cyanoaldehydes, hydrogen, ammonia, optionally water, and optionally one or more solvents into a continuous reductive amination reactor system; (2) contacting said one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig; (3) thereby forming a product mixture comprising one or more cycloaliphatic diamines, optionally one or more bicyclic by-products, optionally one or more cycloaliphatic aminonitriles, optionally one or more cycloaliphatic aminoalcohols, optionally one or more oligomeric by-products, ammonia, water, hydrogen, and optionally one or more solvents; (4) removing said product mixture from the reactor system; (5) removing at least a portion of said ammonia, said hydrogen, or mixture thereof from said product mixture via distillation; (6) removing at least a portion of said water and said one or more optional solvents via distillation; (7) removing at least a portion of one or more optional bicyclic by-products via distillation; (8) removing one or more optional cycloaliphatic aminonitriles, one or more optional cycloaliphatic aminoalcohols, and one or more optional oligomeric by-products via distillation; and (9) thereby separating said one or more cycloaliphatic diamines from said product mixture. One or more aliphatic diamines may also be produced according to the process for separating one or more aliphatic diamines from reductive amination reaction solvents and impurities.

The process for separating one or more aliphatic diamines from reductive amination reaction solvents and impurities may be accomplished via a series of continuous distillation columns or multiple batch distillations. The reaction mixture, as described hereinbelow in further detail, may contain components such as the reaction solvent (for example, methanol, t-butanol, tetrahydrofuran, heptane, isopropylalcohol, mixtures thereof, and combinations thereof), water, bicyclic amine (BA), bicyclic imine (BI), bicyclic diamine (BDA), a mixture of the four diamine isomers (1,3-cis, 1,3-trans, 1,4-cis, and 1,4-trans bis(aminomethyl)cyclohexane), aminonitrile (AN), aminoalcohol (AA), dimers, trimers, and other heavies. Due to the range in boiling points of the impurities, a series of continuous distillation columns or batch distillations operating at various pressures and temperatures is necessary to achieve the desired purity of diamine product. This invention also describes the removal of the BA impurity, which is complicated by the high melting point. The BA separation may be achieved via addition of a co-solvent to keep the BA soluble throughout the distillation. Adding a co-solvent to dissolve the BA impurity eliminates the solid formation in the distillation process, which may cause difficulties in the separation process. Such co-solvents for BA solubility include, but are not limited to, t-butanol, n-butanol, 2-ethoxyethanol, 2-propoxyethanol, hexanol, ethanolamine, BUTYL CELLOSOLVE, octanol, cyclohexylamine, and cyclohexanemethylamine. The BI forms a dimer with the diamine product which may be difficult to remove as an overhead product due to the equilibrium effects and the operating conditions; however, a distillation column side-draw may be employed to remove the BI component. Implementing a side-draw improves the BI separation by forcing the removal of the impurity before it reaches a point in the column where dimer formation reactions begin occurring.

In the alternative, the separation process according to the instant invention may be applied to reaction products that have a multi-component mixture with various physical properties, which require different distillation operating conditions to achieve necessary separation specifications. In another alternative, the separation process according to the instant invention may also be applied when addition of a co-solvent can facilitate the removal of high melting point components, without freezing, from a distillation process. In another alternative, the separation process according to the instant invention may be used during reactive distillations when components can react to form high boilers at lower temperatures (column top or condenser), which could essentially trap the components in the distillation column.

The separation process according to the instant invention provides the option for production of two purity grades of diamine products that are needed for different application products.

The cycloaliphatic diamines include, but are not limited to, the reaction product of one or more cycloaliphatic cyanoaldehydes selected from the group consisting of 3-cyanocyclohexane-1-carboxaldehyde, 4-cyanocyclohexane-1-carboxaldehyde, mixtures thereof, and combinations thereof, hydrogen, and ammonia fed into a reductive amination reactor system, e.g. one or more continuous reactors, one or more batch reactors, one or more semi-batch reactors, or combinations thereof; wherein the one or more cycloaliphatic cyanoaldehydes, hydrogen, and ammonia are contacted with each other in the presence of one or more heterogeneous metal based catalyst systems at a temperature in the range of from 80° C. to about 160° C. and a pressure in the range of from 700 to 3500 psig; and wherein one or more cycloaliphatic diamines are formed; and wherein said one or more cycloaliphatic diamines are selected from the group consisting of 1,3-bis(aminomethyl)cyclohexane, 1,4-bis(aminomethyl)cyclohexane, combinations thereof, and mixtures thereof.

The one or more cycloaliphatic cyanoaldehydes may be selected from the group consisting of 3-cyanocyclohexane carboxaldehyde, 4-cyanocyclohexane carboxaldehyde, mixtures thereof, and combinations thereof.

3-cyanocyclohexane carboxaldehyde, CAS No. 50738-61-9, may have the following structure and formula:

$C_8H_{11}NO$
Mol. Wt.: 137.179

4-cyanocyclohexane carboxaldehyde, CAS No. 18214-33-0, may have the following structure and formula:

$C_8H_{11}NO$
Mol. Wt.: 137.179

The reaction between one or more cycloaliphatic cyanoaldehydes, hydrogen, and ammonia may take place in the presence of one or more heterogeneous metal based catalyst systems at a temperature in the range of from 60° C. to 200° C., for example from 80° C. to about 160° C. or from 90° C. to about 130° C., and a pressure in the range of from 500 to 5000 psig, for example from 700 to 3500 psig or from 1400 to 2500 psig. Such one or more heterogeneous metal based catalyst systems may comprise a metal selected from the group consisting of Co, Ni, Ru, Fe, Cu, Re, Pd, oxides thereof, mixtures thereof, and combinations thereof. Such one or more heterogeneous metal based catalyst systems may comprise a bulk metal catalyst system, sponge-metal catalyst system, supported metal catalyst system, mixtures thereof, or combinations thereof. Such one or more heterogeneous metal based catalyst systems may comprise a bulk Co based catalyst system. In a continuous process, the catalyst lifetime facilitates a weight ratio of the one or more cycloaliphatic diamines to one or more heterogeneous metal based catalyst systems that is greater than 300; for example, greater than 500; or in the alternative greater than 900; or in the alternative greater than 1000. The one or more heterogeneous metal based catalyst systems may further comprise a sponge-metal catalyst. The one or more heterogeneous metal based catalyst systems may further comprise one or more promoters or one or more binding agents. Such one or more promoters may be selected from the group consisting of alkali metals, and alkaline earth metals. Such one or more binding agents may comprise silicon oxide, aluminum oxide, titanium oxide, zirconium oxide, mixtures thereof, or combinations thereof. The one or more heterogeneous metal based catalyst systems may further comprise one or more catalyst supports. Such one or more catalyst supports may comprise silicon oxide, aluminum oxide, titanium oxide, zirconium oxide, mixtures thereof, or combinations thereof. Such one or more heterogeneous metal based catalyst systems are commercially available as Raney Cobalt Catalyst from Grace Davison Catalyst Company, Co-0179T cobalt catalyst from BASF, and Co-138E cobalt catalyst from BASF, and G-103 cobalt catalyst from Süd-Chemie.

In a continuous process, the cost of the catalyst depends on its lifetime, which is equivalent to the weight of product produced per pound of catalyst required. An adequately long lifetime is required for an economically viable continuous process. The one or more heterogeneous metal based catalyst systems may be present in an amount necessary to catalyze the reaction between the one or more cycloaliphatic cyanoaldehydes, hydrogen, and ammonia. For example, the catalyst lifetime facilitates a weight ratio of the cycloaliphatic diamines to the one or more heterogeneous metal based catalyst systems to be greater than 300, for example, greater than 500; or in the alternative, greater than 900; or in the alternative, greater than 1000. In one embodiment, the one or more heterogeneous metal based catalyst systems may, for example, comprise a continuous fixed bed catalyst system.

The one or more heterogeneous metal based catalyst systems may be present in an amount necessary to catalyze the reaction between the one or more cycloaliphatic cyanoaldehydes, hydrogen, and ammonia. The space velocity, which is defined as mass of one or more cycloaliphatic cyanoaldehydes mixture per mass of catalyst per hour, is in the range of from 0.1 to 10.0 per hour; for example, from 0.1 to 5.0 per hour; or in the alternative, from 0.1 to 3.0 per hour; or in the alternative, from 0.1 to 2.0 per hour; or in the alternative, from 0.1 to 1.0 per hour; or in the alternative, from 0.3 to 0.8 per hour.

Ammonia is present in excess amount relative to the one or more cycloaliphatic cyanoaldehydes. Ammonia may, for example, be present in a range of 2 to 50 moles per mole of one or more cycloaliphatic cyanoaldehydes; or in the alternative, in a range of 5 to 40 moles per mole of one or more cycloaliphatic cyanoaldehydes; or in the alternative, in a range of 8 to 30 moles per mole of one or more cycloaliphatic cyanoaldehydes. Hydrogen may, for example, be present in a range of 3 to 30 moles per mole of one or more cycloaliphatic cyanoaldehydes; or in the alternative, in a range of 3 to 10 moles per mole of one or more cycloaliphatic cyanoaldehydes; or in the alternative, in a range of 3 to 6 moles per mole of one or more cycloaliphatic cyanoaldehydes.

The reaction between one or more cycloaliphatic cyanoaldehydes, hydrogen, and ammonia may optionally take place in the presence of one or more solvents. Such solvents include, but are not limited to, water; 2-propanol (isopropylalcohol), CAS No. 67-63-0; methanol, CAS No. 67-56-1; t-butanol, CAS No. 75-65-0; and tetrahydrofuran (THF), CAS No. 109-99-9. The feed into the reactor may comprise 0 to 90 percent by weight of one or more solvents, based on the combined weight of one or more cycloaliphatic cyanoaldehydes and the one or more solvents; or in the alternative, 0 to 30 percent by weight of one or more solvents, based on the combined weight of one or more cycloaliphatic cyanoaldehydes and the one or more solvents; or in the alternative, 0 to 10 percent by weight of one or more solvents, based on the combined weight of one or more cycloaliphatic cyanoaldehydes and the one or more solvents.

The reaction between one or more cycloaliphatic cyanoaldehydes, hydrogen, and ammonia may take place in a continuous reductive amination reactor system; or in the alternative, it may take place in a batch reactor system; or in the alternative, it may take place in a semi-batch reactor system. Such reactor systems are generally known to a person of ordinary skill in the art. The continuous reductive amination reactor system, the semi-batch reductive amination reactor system, or the batch reductive amination reactor system may comprise one or more reactors in series, in parallel, or combinations thereof.

The one or more cycloaliphatic diamines produced according to the instant invention may be selected from the group consisting of 1,3-bis(aminomethyl)cyclohexane, 1,4-bis(aminomethyl)cyclohexane, combinations thereof, and mixtures thereof.

1,3-bis(aminomethyl)cyclohexane, CAS No. 2579-20-6, may have the following structure or formula:

$C_8H_{18}N_2$
Mol. Wt.: 142.242

1,4-bis(aminomethyl)cyclohexane, CAS No. 2549-93-1, may have the following structure or formula:

$C_8H_{18}N_2$
Mol. Wt.: 142.242

Additional byproducts may include 3-(aminomethyl)-cyclohexanecarbonitrile, CAS No. 23083-50-3; 4-(aminomethyl)-cyclohexanecarbonitrile, CAS No. 54898-73-6; 3-azabicyclo[3.3.1]nonane, CAS No. 280-70-6; 3-azabicyclo[3.3.1]non-2-ene, CAS No. 7129-32-0; 7-amino-bicyclo[2.2.1]heptane-1-methanamine; 3-(aminomethyl)-cyclohexanemethanol, CAS No. 925921-54-6; 4-(aminomethyl)-cyclohexanemethanol, CAS No. 1074-62-0.

The process for producing cycloaliphatic diamines may comprise the steps of (1) feeding one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, and ammonia into a reductive amination reactor system; (2) contacting the one or more cycloaliphatic cyanoaldehydes, hydrogen, and ammonia with each other in the presence of one or more heterogeneous metal based catalyst systems at a temperature in the range of from 80° C. to about 160° C. and a pressure in the range of from 700 to 3500 psig; and (3) thereby forming one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

In a process for producing cycloaliphatic diamines, one or more cycloaliphatic cyanoaldehydes, hydrogen, ammonia, optionally water, and optionally one or more solvents are introduced into a reductive amination reactor system and reacted with each other in the presence of one or more heterogeneous metal based catalyst systems at a temperature in the range of from 80° C. to about 160° C. and a pressure in the range of from 700 to 3500 psig to yield one or more cycloaliphatic diamines.

In one embodiment, one or more cycloaliphatic cyanoaldehydes are contacted with ammonia first and then the product mixture including the product of the reaction of one or more cycloaliphatic cyanoaldehydes with ammonia is contacted with hydrogen in the presence of one or more heterogeneous metal based catalyst systems.

A product mixture including one or more aliphatic diamines, optionally a portion of the product of the reaction of one or more cycloaliphatic cyanoaldehydes with ammonia, optionally a portion of the ammonia, optionally a portion of the hydrogen, optionally a portion of one or more by-products, optionally a portion of the water, and optionally a portion of the one or more solvents is formed in the one or more reactor systems, as described hereinabove. The product mixture is then removed from the one or more reactor systems and transferred to one or more distillation columns arranged in sequential order. After the product mixture is transferred to one or more distillation columns arranged in sequential order, at least a portion of the ammonia, a portion of the hydrogen, or mixture thereof is removed from the product mixture via one or more distillation steps. Subsequently, at least a portion of the one or more solvents, if optionally present, and/or water is removed via one or more distillation steps. Subsequently, at least a portion of the product of the reaction of one or more cycloaliphatic cyanoaldehydes with ammonia or one or more by-products is removed via one or more distillation steps, thus separating the one or more aliphatic diamines from the product mixture and converting the one or more cyanoaldehydes to one or more aliphatic diamines.

Referring to FIGS. 1-4, a series of diagrams illustrate alternative distillation schemes as examples; however, these alternative distillation schemes should not be considered to be the only schemes encompassed by the claims of this disclosure. Combinations (hybrids) and permutations of the alternative distillation schemes are further included.

In one embodiment, a first distillation column, operating at pressure in the range of at least 200 mmHg to atmospheric, facilitates the removal of lights and BA (with the addition of one or more co-solvents, as described above). A second distillation column, operating at pressure in the range of from 0.1 to 50 mmHg, facilitates the removal heavies, i.e., AN, AA, dimers, trimers, and trace heavies. A third distillation column, operating at pressure in the range of from 0.1 to 200 mmHg, facilitates the removal of low purity diamine fraction (for example, greater than 85 weight percent diamine) and high purity diamine fraction (for example, greater than 99 weight percent diamine) and removal of BI via a side-draw.

In another embodiment, a first distillation column, operating at pressure in the range of at least 50 to 300 mmHg, facilitates the removal of $H_2$ (at about 175 psig) and ammonia (at about less than 150 psig). A second distillation column, operating at pressure in the range of from 200 to 760 mmHg, facilitates the removal of lights (approximately 100 weight percent) and greater than 90 weight percent of BA (with the addition of one or more co-solvents, as described above). A third distillation column, operating at pressure in the range from 0.1 to 50 mmHg, facilitates the removal heavies, i.e., AN, AA, dimers, trimers and trace heavies. A fourth distillation column, operating at pressure in the range of from 0.1 to 300 mmHg, facilitates the removal of low purity diamine fraction (for example, greater than 85 weight percent diamine) and high purity diamine fraction (for example, greater than 99 weight percent diamine), with removal of BI via a side-draw.

Depending on the composition of the reaction mixture and product specifications, the number of columns and order of removal of components could be rearranged. For example, in the first distillation column, only lights may be removed, leaving BA in the mixture to be included in the low purity product to be removed in the third distillation column. The three distillation column model, described above, may, for example, be suitable for the expected reaction mixtures with the low purity and high purity diamine product specification requirements.

Figure 1:
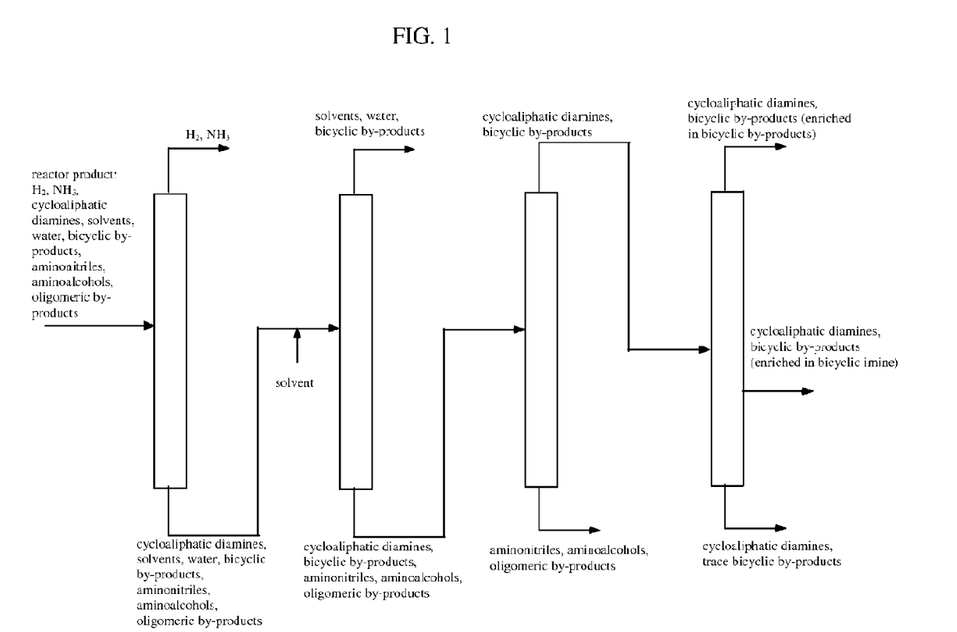
FIG. 1 is a first schematic illustrating a first embodiment of the process for separating one or more aliphatic diamines from reductive amination reaction solvents and impurities.

Referring to FIG. 1, a series of distillation steps provides two different grades of final product: the overheads stream from the last column is the low purity grade, and the bottoms stream is the high purity grade.

Figure 2:
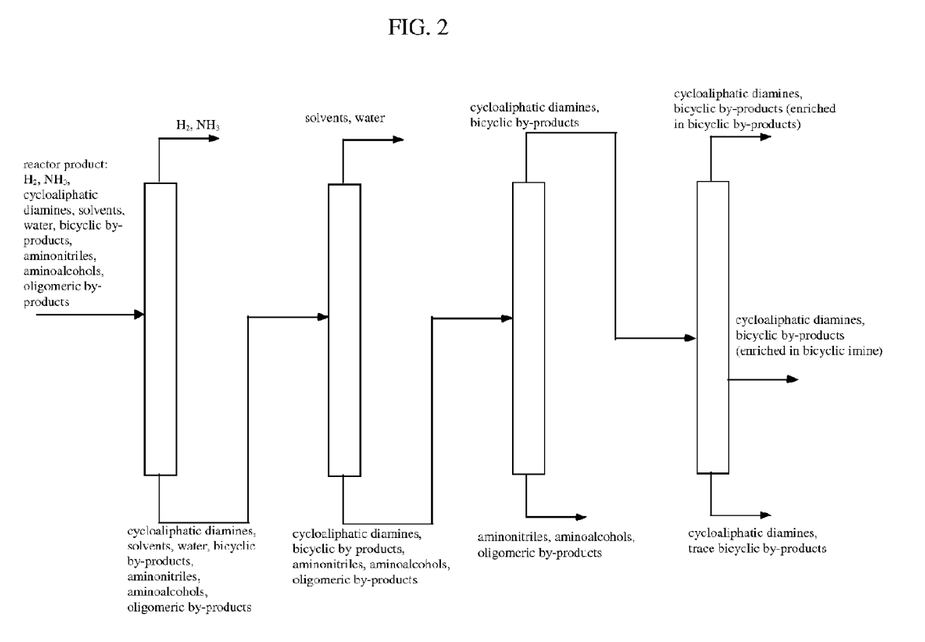
FIG. 2 is a second schematic illustrating a second embodiment of the process for separating one or more aliphatic diamines from reductive amination reaction solvents and impurities.

Referring to FIG. 2, an alternative series of distillation steps provides two different grades of final product: the overheads stream from the last column is the low purity grade, and the bottoms stream is the high purity grade. In this alternative, bicyclic amine by-product is not separated but is included in the low purity grade product.

Figure 3:
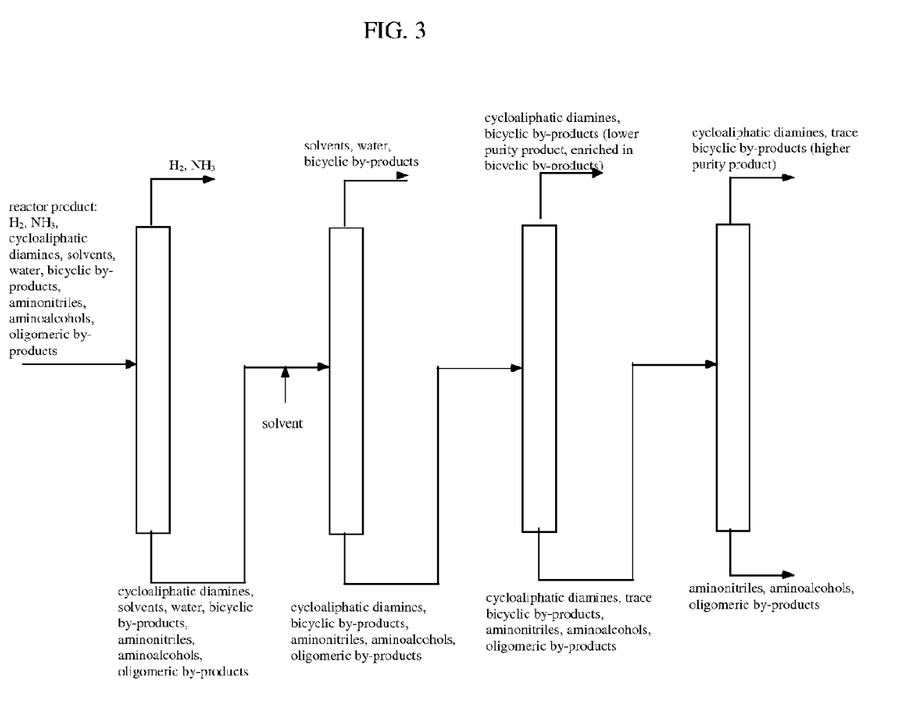
FIG. 3 is a third schematic illustrating a third embodiment of the process for separating one or more aliphatic diamines from reductive amination reaction solvents and impurities.

Referring to FIG. 3, an alternative series of distillation steps, in which the low purity grade product is removed prior to the last column, is illustrated. The heavy by-products and high purity grade product are then separated in the final column.

Figure 4:
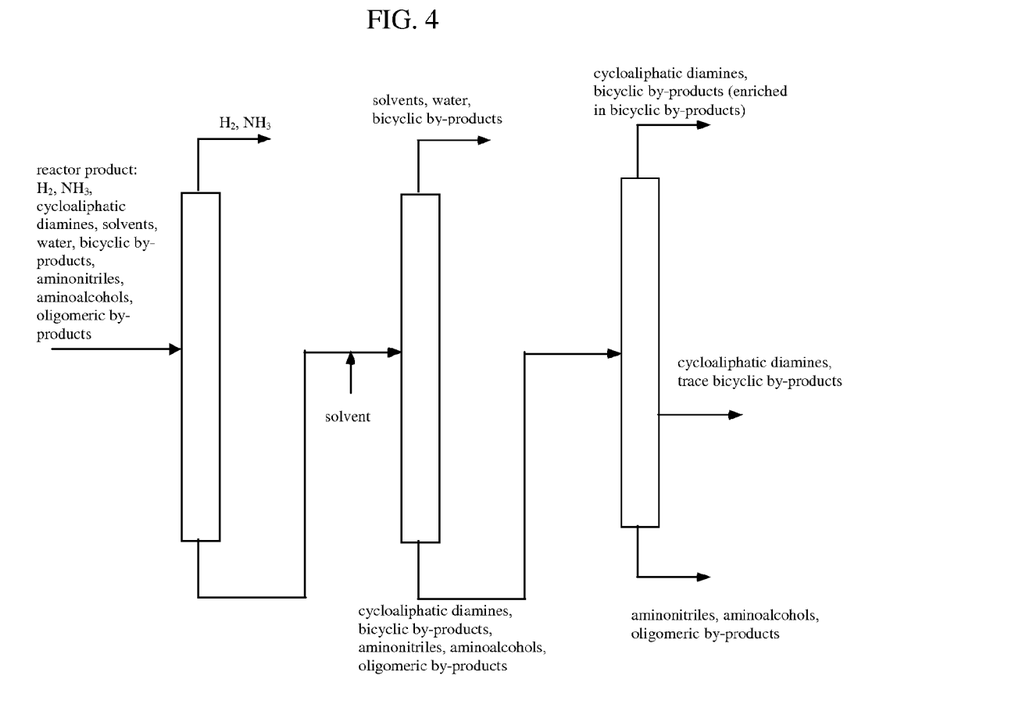
FIG. 4 is fourth schematic illustrating a fourth embodiment of the process for separating one or more aliphatic diamines from reductive amination reaction solvents and impurities.

Referring to FIG. 4, an alternative series of distillation steps, in which the separate heavies removal column is eliminated, is illustrated. In this case, no bicyclics are removed in the side-draw from the last column. The function of the last two columns of the first distillation scheme, as shown in FIG. 1, may, for example, be accomplished in a single column with a side-draw or in a dividing wall column, as shown in the three streams illustrated schematically in FIG. 4.

The one or more cycloaliphatic diamines produced according to the instant invention may be used as a precursor to an aliphatic diisocyanate (bis(isocyanatomethyl)cyclohexane), as a chain extender in certain polyurethanes systems, or as an epoxy curing agent.

EXAMPLES

The following examples illustrate the present invention but are not intended to limit the scope of the invention.
Sample Mixtures 1-4
Sample mixtures 1-4 were provided. The weight fractions of cycloaliphatic components of sample mixtures 1-4 are reported on a solvent free basis in Table I. The feed mixture contained approximately 33 percent solvents, e.g., methanol, t-butanol, isopropanol, or tetrahydrofuran.
Distillation Process and Equipment
The distillation process was conducted according to the following procedures. Approximately 10 kg of combination of sample mixtures 1-4 was loaded in the distillation system described below. The distillation system comprised a 2 inch by 6 ft packed distillation tower, with Intalox® Saddles (0.25 inch ceramic) distillation packing and an 11 liter reboiler in a batch operation. The distillation system included feed/thermowell ports every 7.5 inches up the column and heat tape tracing with insulation for adiabatic operation. The reboiler heater was capable of providing heat in a temperature range of 20 to 200° C., and the condenser cooler was capable of removing heat in temperature in the range of −25 to 150° C. The vacuum capability was approximately 760 to 0.1 mmHg. The sampling was manual, and Camile™ provided control and data collection.

A batch distillation was conducted over 2 days, where 14 overhead cuts were taken and analyzed by gas chromatography. The analytical and process conditions are reported in Table II.

The present invention may be embodied in other forms without departing from the spirit and the essential attributes thereof, and, accordingly, reference should be made to the appended claims, rather than to the foregoing specification, as indicating the scope of the invention.

TABLE I

Feed - Weight Percent Product and By-Products (normalized to not include solvents and trace impurities)

| Sample Mixture No. | Diamine | Bicyclic Amine | Bicyclic Imine | Bicyclic Imine 2 | Bicyclic Diamine | Amino Alcohol | Aminonitrile |
|---|---|---|---|---|---|---|---|
| 1 | 72.06% | 6.34% | 0.61% | 0.08% | 0.27% | 0.77% | 15.24% |
| 2 | 79.30% | 7.27% | 0.38% | 0.07% | 0.04% | 0.33% | 8.89% |
| 3 | 76.52% | 6.44% | 0.39% | 0.06% | 0.04% | 0.53% | 12.31% |
| 4 | 88.91% | 2.95% | 0.39% | 0.15% | 0.16% | 0.51% | 3.14% |

TABLE II

Analytical GC Results (wt %) and Operating Conditions for ADID Batch Distillation

|  | Cut 1 | Cut 2 | Cut 3 | Cut 4 | Cut 5 | Cut 6 | Cut 7 |  |
|---|---|---|---|---|---|---|---|---|
| Methanol | 0.3% | 0.3% | 0.3% | 0.3% | 45.9% | 46.7% | 45.1% | overnight |
| IPA | 1.0% | 1.4% | 1.8% | 1.8% | 0.7% | 0.7% | 0.0% | shutdown |
| t-butanol | 58.2% | 77.1% | 88.9% | 86.2% | 22.3% | 22.6% | 0.3% | |
| THF | 40.2% | 21.2% | 5.4% | 4.0% | 0.4% | 0.4% | 0.1% | |
| Cyclohexanemethylamine | 0.0% | 0.0% | 0.3% | 1.2% | 5.2% | 5.3% | 9.6% | |
| Cyclohexenemethylamine | 0.0% | 0.0% | 0.1% | 0.2% | 1.6% | 1.7% | 9.5% | |
| Bicyclic amine | 0.0% | 0.0% | 1.6% | 5.0% | 22.5% | 22.8% | 30.9% | |
| Cyanocyclohexane | 0.0% | 0.0% | 0.0% | 0.0% | 0.0% | 0.0% | 0.9% | |
| Cyanocyclohexene | 0.0% | 0.0% | 0.0% | 0.0% | 0.0% | 0.0% | 0.8% | |
| Bicyclic imine | 0.0% | 0.0% | 0.0% | 0.0% | 0.0% | 0.0% | 0.5% | |
| Bicyclic diamine | 0.0% | 0.0% | 0.0% | 0.0% | 0.0% | 0.0% | 0.0% | |
| 1,3 C diamine | 0.0% | 0.0% | 0.0% | 0.0% | 0.0% | 0.0% | 0.0% | |
| 1,4 T diamine | 0.0% | 0.0% | 0.0% | 0.0% | 0.0% | 0.0% | 0.0% | |
| 1,3 T diamine | 0.0% | 0.0% | 0.0% | 0.0% | 0.0% | 0.0% | 0.0% | |
| 1,4 C diamine | 0.0% | 0.0% | 0.0% | 0.0% | 0.0% | 0.0% | 0.0% | |
| 1,4 amino-nitrile | 0.0% | 0.0% | 0.0% | 0.0% | 0.0% | 0.0% | 0.0% | |
| 1,3 amino-nitrile | 0.0% | 0.0% | 0.0% | 0.0% | 0.0% | 0.0% | 0.0% | |
| Total DA | 0.0% | 0.0% | 0.0% | 0.0% | 0.0% | 0.0% | 0.0% | |
| Total | 99.7% | 99.9% | 98.4% | 98.8% | 98.6% | 100.2% | 97.7% | |
| Mass of Cut (g) | 815 | 786 | 783 | 379 | 858 | 585 | 894 | |
| Pressure (mmHg) | 300 | 300 | 300 | 300 | 270 | 170 | 130 | |
| Reboiler heater setpoint (° C.) | 140 | 140 | 140 | 140 | 180 | 200 | 200 | |
| Still pot temp (° C.) | 78.0 | 84.5 | 112.9 | 115.1 | 150.0 | 157.0 | 164.3 | |
| Overhead vapor temp (° C.) | 54.4 | 53.8 | 66.6 | 65.0 | 47.1 | 33.2 | 57.9 | |

Analytical GC Results (wt %) and Operating Conditions for ADID Batch Distillation

|  | Cut 8 | Cut 9 | Cut 10 | Cut 11 | Cut 12 | Cut 13* | Cut 14 |
|---|---|---|---|---|---|---|---|
| Methanol | 0.0% | 0.0% | 0.0% | 0.0% | 0.0% | 0.0% | 0.0% |
| IPA | 0.0% | 0.0% | 0.0% | 0.0% | 0.0% | 0.0% | 0.0% |
| t-butanol | 0.0% | 0.0% | 0.0% | 0.0% | 0.0% | 0.0% | 0.0% |
| THF | 0.0% | 0.0% | 0.0% | 0.0% | 0.0% | 0.0% | 0.0% |
| Cyclohexanemethylamine | 1.0% | 0.4% | 0.1% | 0.3% | 0.3% | 0.3% | 0.3% |
| Cyclohexenemethylamine | 0.2% | 0.1% | 0.0% | 0.1% | 0.0% | 0.0% | 0.0% |
| Bicyclic amine | 19.7% | 7.8% | 1.2% | 0.2% | 0.0% | 0.0% | 0.0% |
| Cyanocyclohexane | 2.4% | 1.0% | 0.2% | 0.0% | 0.0% | 0.0% | 0.0% |
| Cyanocyclohexene | 3.3% | 1.3% | 0.2% | 0.0% | 0.0% | 0.0% | 0.0% |
| Bicyclic imine | 3.7% | 1.9% | 0.9% | 0.5% | 0.2% | 0.1% | 0.2% |
| Bicyclic diamine | 0.3% | 0.1% | 0.1% | 0.0% | 0.0% | 0.0% | 0.0% |
| 1,3 C diamine | 20.5% | 24.9% | 26.1% | 25.3% | 24.4% | 22.4% | 19.7% |
| 1,4 T diamine | 21.5% | 26.3% | 28.0% | 27.4% | 26.7% | 24.9% | 22.3% |
| 1,3 T diamine | 19.1% | 24.8% | 28.5% | 29.3% | 29.5% | 29.0% | 27.1% |
| 1,4 C diamine | 7.6% | 10.6% | 13.4% | 14.7% | 15.5% | 16.4% | 16.2% |

TABLE II-continued

|  | | | | | | | |
|---|---|---|---|---|---|---|---|
| 1,4 amino-nitrile | 0.1% | 0.3% | 0.7% | 1.3% | 2.1% | 4.7% | 9.6% |
| 1,3 amino-nitrile | 0.0% | 0.1% | 0.2% | 0.3% | 0.6% | 1.7% | 3.9% |
| Total DA | 68.7% | 86.6% | 96.0% | 96.7% | 96.2% | 92.6% | 85.4% |
| Total | 99.6% | 99.6% | 99.5% | 99.5% | 99.5% | 99.5% | 99.5% |
| Mass of Cut (g) | 108.5 | 116 | 252.7 | 885.8 | 886.4 | 895.7 | 828.2 |
| Pressure (mmHg) | 50 | 50 | 50 | 50 | 50 | 50 | 2.5 |
| Reboiler heater setpoint (° C.) | 200 | 200 | 200 | 200 | 200 | 200 | 200 |
| Still pot temp (° C.) | 173.8 | 174.2 | 174.4 | 175.4 | 177.2 | 183.1 | 178.0 |
| Overhead vapor temp (° C.) | 138.2 | 140.2 | 144.0 | 145.3 | 145.5 | 137.0 | 97.7 |

*During cut 13 the boilup rate dramatically decreased, due to lack of driving force to boil the pot contents. The pressure was lowered and the distillation resumed.

We claim:

1. A process for separating one or more aliphatic diamines from reductive amination reaction solvents and impurities comprising the steps of:
    feeding one or more cycloaliphatic cyanoaldehydes selected from the group consisting of 1,3-cyanocyclohexane carboxaldehyde, 1,4-cyanocyclohexane carboxaldehyde, mixtures thereof, and combinations thereof, hydrogen, ammonia, optionally water, and optionally one or more solvents into a reductive amination reactor system;
    contacting said one or more cycloaliphatic cyanoaldehydes, hydrogen, and ammonia with each other in the presence of one or more heterogeneous metal based catalyst systems comprise a metal selected from the group consisting of Co, Ni, Ru, Fe, Cu, Re, Pd, oxides thereof, mixtures thereof, and combinations thereof at a temperature in the range of from 80° C. to about 160° C. and a pressure in the range of from 700 to 3500 psig;
    thereby forming a product mixture comprising one or more cycloaliphatic diamines selected from the group consisting of 1,3-bis(aminomethyl)cyclohexane, 1,4-bis(aminomethyl)cyclohexane, combinations thereof, and mixtures thereof, one or more bicyclic amine by-products, optionally one or more cycloaliphatic aminonitriles, optionally one or more cycloaliphatic aminoalcohols, optionally one or more oligomeric by-products, ammonia, water, hydrogen, and optionally one or more solvents;
    removing said product mixture from the reactor system;
    adding a co-solvent for said one or more bicyclic amine by-products to said product mixture;
    removing at least a portion of said ammonia, said hydrogen, or mixture thereof from said product mixture via distillation;
    removing at least a portion of said water and said one or more optional solvents via distillation;
    removing at least a portion of said one or more bicyclic amine by-products via distillation;
    removing one or more optional cycloaliphatic aminonitriles, one or more optional cycloaliphatic aminoalcohols, and one or more optional oligomeric by-products via distillation;
    thereby separating said one or more cycloaliphatic diamines from said product mixture;
    wherein said distillation comprises employing a first distillation column, operating at pressure in the range of at least 200 mmHg to atmospheric, for removing at least a portion of said ammonia, said hydrogen, said water, said one or more bicyclic amine, and said one or more co-solvents; employing a second distillation column operating at pressure in the range of from 0.1 to 50 mmHg for removing aminonitriles, aminoalcohols, dimers, trimers; and employing a third distillation column, operating at pressure in the range of from 0.1 to 200 mmHg, for removing a low purity diamine fraction having greater than 85 weight percent diamine and high purity diamine fraction having greater than 99 weight percent diamine, and for removing of any bicyclic imine via a side-draw.

2. The process of claim 1, wherein said one or more heterogeneous metal based catalyst systems is a bulk metal catalyst system, sponge-metal catalyst system, supported metal catalyst system, mixtures thereof, or combinations thereof.

3. The process of claim 1, wherein said one or more heterogeneous metal based catalyst systems comprises a bulk Co based catalyst system.

4. The process of claim 1, wherein said one or more heterogeneous metal based catalyst systems further comprises one or more promoters, one or more binding agents, or one or more catalyst supports.

5. The process of claim 4, wherein said one or more promoters are selected from the group consisting of alkali metals, and alkaline earth metals.

6. The process of claim 4, wherein said one or more binding agents comprise silicon oxide, aluminum oxide, titanium oxide, zirconium oxide, mixtures thereof, or combinations thereof.

7. The process of claim 4, wherein said one or more catalyst supports comprise silicon oxide, aluminum oxide, titanium oxide, zirconium oxide, mixtures thereof, or combinations thereof.

8. The process according to claim 1, wherein said catalyst system has a space velocity in the range of from 0.1 to 10.0 per hour, wherein space velocity is defined as the ratio of the mass of the mixture of one or more cycloaliphatic cyanoaldehydes to the mass of catalyst per hour.

9. The process according to claim 1, wherein the catalyst lifetime facilitates a weight ratio of said one or more cycloaliphatic diamines to said one or more heterogeneous metal based catalyst systems that is greater than 300.

10. The process of claim 1, wherein said reductive amination reactor system comprises one or more continuous reactors, batch reactors, semi-batch reactors, or combinations thereof connected in series, in parallel, or combinations thereof.

* * * * *